(12) United States Patent
Yagi et al.

(10) Patent No.: US 8,758,684 B2
(45) Date of Patent: Jun. 24, 2014

(54) AUTOMATIC ANALYZER

(75) Inventors: Kenichi Yagi, Mito (JP); Takayuki Noda, Hitachinaka (JP); Kenichi Takahashi, Naka (JP); Kenji Teshigawara, Hitachinaka (JP); Atsushi Suzuki, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1074 days.

(21) Appl. No.: 11/833,650

(22) Filed: Aug. 3, 2007

(65) Prior Publication Data

US 2008/0310999 A1 Dec. 18, 2008

(30) Foreign Application Priority Data

Aug. 4, 2006 (JP) .................................. 2006-213257

(51) Int. Cl.
*G01N 35/02* (2006.01)
*G01N 35/00* (2006.01)

(52) U.S. Cl.
CPC .......... *G01N 35/00603* (2013.01); *G01N 35/02* (2013.01)
USPC .................. 422/65; 422/63; 436/47

(58) Field of Classification Search
CPC ............................................... G01N 35/00603
See application file for complete search history.

(56) References Cited

U.S. PATENT DOCUMENTS

| 5,902,549 A * | 5/1999 | Mimura et al. ................. 422/65 |
| 5,972,295 A * | 10/1999 | Hanawa et al. ................. 422/65 |
| 2002/0016683 A1 * | 2/2002 | Shiba et al. ..................... 702/22 |
| 2003/0235514 A1 * | 12/2003 | Nogawa et al. ................. 422/65 |
| 2004/0091396 A1 * | 5/2004 | Nakamura et al. .............. 422/65 |
| 2005/0207938 A1 * | 9/2005 | Hanawa et al. ................. 422/64 |

FOREIGN PATENT DOCUMENTS

| EP | 0 795 754 A2 | 9/1997 |
| EP | 0 856 736 A2 | 8/1998 |
| EP | 1 498 734 A1 | 1/2005 |
| JP | 63-271164 A | 11/1988 |
| JP | 2001-091519 | 4/2001 |
| JP | 2002-022748 | 1/2002 |

* cited by examiner

*Primary Examiner* — P. Kathryn Wright
(74) *Attorney, Agent, or Firm* — Mattingly & Malur, PC

(57) ABSTRACT

An automatic analysis system, which is capable of quickly performing reinspection, includes a sample rack which holds a sample vessel containing a sample; a sample rack input unit in which the sample rack is input; a carrier line which carries the sample rack; a plurality of automatic analyzers arranged along the carrier line; a sample rack holding unit which holds the sample rack storing an analyzed sample; a sample rack collection unit which collects the sample rack storing an analyzed sample; a carrier line for reinspection which returns the sample rack containing a sample subjected to reinspection depending on analysis results; and a controller for returning the sample rack from the sample rack holding unit through the carrier line for reinspection and controlling any one of automatic analyzers different from one that has previously performed analysis to perform reanalysis of the sample.

1 Claim, 10 Drawing Sheets

AUTOMATIC ANALYZER

BACKGROUND OF THE INVENTION

1. Field of the Invention

The present invention relates to an automatic analysis system which performs qualitative and quantitative analyses of a biological sample, such as blood, urine, etc. More particularly, the present invention relates to an automatic analysis system which is provided with a reinspection function.

2. Description of the Related Art

With an automatic analyzer, analysis results largely depend on components and conditions of a sample under analysis. Then, if analysis results are judged to be abnormal through comparison with a normal value, the sample is reanalyzed to recheck whether any component value of the sample is abnormal.

A method of determining reinspection and a method of performing reinspection are disclosed in, for example, JP-A-2001-91519, JP-A-2002-22748, etc.

SUMMARY OF THE INVENTION

In many cases, an abnormal value obtained from measurement and analysis results is attributed to an actual abnormal value of a component of a sample under inspection.

In some cases, however, an abnormal value is attributed to the reagent and apparatus, for example, a degraded or contaminated reagent, a defective sample dispenser, a reagent supply unit, or a measurement unit, as well as aging thereof.

Therefore, even if analysis results are judged to be abnormal through comparison with a normal value and then the sample is reanalyzed using the same analyzer, abnormal results may be outputted again because of reagent or apparatus.

As a result, it becomes difficult to determine which of the sample component, reagent, and apparatus has caused the abnormal value.

In order to determine the cause of the abnormal value, an operator may perform analysis by bringing the sample to another analyzer. In this case, however, the amount of works increases and it takes much time to obtain results of the sample, remarkably reducing the efficiency of analytical processing of the sample.

An object of the present invention is to provide an automatic analysis system that is capable of coping with the above-mentioned problem and quickly performing reinspection.

The present invention is an automatic analysis system comprising: a sample rack which holds a sample vessel containing a sample; a carrier line which carries the above-mentioned sample rack; and a plurality of automatic analyzers arranged along the above-mentioned carrier line; the automatic analysis system including control means for controlling any one of automatic analyzers, different from one that has previously been used, to perform reanalysis of the above-mentioned sample.

The present invention is an automatic analysis system comprising: a sample vessel which contains a sample; a plurality of reagent vessels which contain a reagent; a plurality of reaction units; a plurality of sample dispensing means for dispensing a sample from the above-mentioned sample vessel to the above-mentioned reaction units; and a plurality of reagent dispensing means for dispensing an inspection reagent from the above-mentioned reagent vessels to the above-mentioned reaction units; the automatic analysis system including control means for controlling an automatic analyzer to perform reanalysis of the above-mentioned sample by use of a reagent in a reagent vessel different from the above-mentioned one, the above-mentioned sample dispensing means, and the above-mentioned reagent dispensing means that have previously been used.

In accordance with the present invention, it is possible to perform reinspection quickly.

DETAILED DESCRIPTION OF PREFERRED EMBODIMENTS

Embodiments of the present invention will be explained below with reference to the accompanying drawings.

An overall configuration of an automatic analysis system according to the present embodiment will be explained with reference to FIG. 1.

Figure 1:
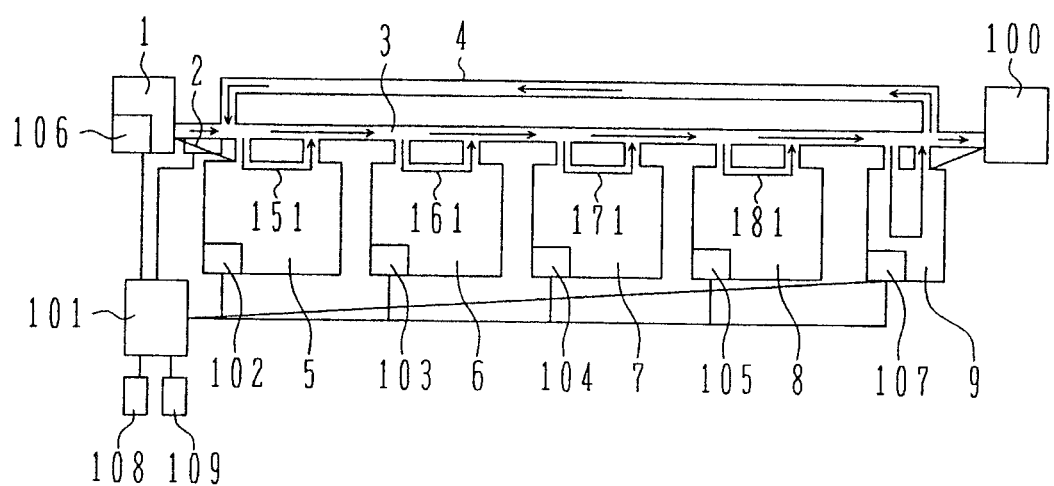
FIG. 1 is a system block diagram showing an overall configuration of an automatic analysis system according to an embodiment of the present invention.

FIG. 1 is a system block diagram showing an overall configuration of the automatic analysis system according to an embodiment of the present invention.

The automatic analysis system according to the present embodiment includes a sample rack input unit 1, an ID reader 2, a carrier line 3, a reinspection carrier line 4, analysis modules 5, 6, 7, and 8 which are automatic analyzers, a sample rack holding unit 9, a sample rack collection unit 100, and a total management computer 101.

The analysis modules 5, 6, 7, and 8 are the same automatic analyzers. The plurality of automatic analyzers are arranged along the carrier line 3.

The sample rack input unit 1 is used to input a plurality of sample racks that hold a plurality of sample vessels each containing a plurality of samples.

The analysis modules 5, 6, 7, and 8 (automatic analyzers) are arranged along the carrier line 3 and removably connected to the carrier line 3. There may be any number of analysis modules. The present embodiment includes four analysis modules.

With the present embodiment, a case where all analysis modules are biochemical analysis modules will be explained below.

It may be possible that the analysis modules be configured in combination with other analysis modules, such as a biochemical analysis module, an immunity analysis module, and an electrolyte analysis module.

The carrier line 3 carries a sample rack from the sample rack input unit 1 to a predetermined analysis module of the analysis modules 5, 6, 7, and 8.

Then, the carrier line 3 carries the sample rack holding a sample that has been analyzed by any one of the analysis modules 5, 6, 7, and 8 so as to store it in the sample rack collection unit 100.

The analysis modules 5, 6, 7, and 8 include incoming lines 151, 161, 171, and 181, respectively.

A sample rack is carried from the carrier line 3 to the analysis modules 5, 6, 7, and 8 by guiding it to the incoming lines 151, 161, 171, and 181, respectively.

If a sample that has been analyzed by any one of the analysis modules 5, 6, 7, and 8 needs to be reinspected or further analyzed by another analysis module, the reinspection carrier line 4 returns the relevant sample rack to an entrance of the carrier line 3.

If a sample that has been analyzed by each analysis module is to be further analyzed by another analysis module, the sample rack holding unit 9 temporarily holds the relevant sample rack until determination is made of whether the sample needs to be reinspected after completion of dispensing and analysis by each analysis module.

The analysis modules 5, 6, 7, and 8 respectively include computers 102, 103, 104, and 105 that perform control for necessary processing in the respective analysis module.

The sample rack input unit 1 includes a computer 106 that performs necessary control for the sample rack input unit 1, the carrier line 3, and the reinspection carrier line 4, and in the sample rack collection unit 100.

Furthermore, the sample rack holding unit 9 includes a computer 107 that performs necessary control in the sample rack. The computers 102, 103, 104, 105, 106, and 107 and the ID reader 2 are connected to the total management computer 101.

An operation unit 108 for inputting necessary information and a display unit 109 for displaying analysis results are further connected to the computer 101. Diverse control operations of the automatic analysis system and the analysis modules are performed through control means including the computers 101, 102, 103, 104, 105, 106, and 107.

A sample vessel held by the sample rack has a sample ID which indicates sample-related information (receipt number, patient name, requested analysis item, etc.), and the sample rack has a rack ID which indicates rack identification information, such as rack number.

The sample rack placed in the sample rack input unit 1 is carried by the carrier line 3. When the sample rack is moved on the carrier line 3, the sample ID and the sample rack ID are read by the ID reader 2 and then transferred to the computer 101.

Based on the above-mentioned information, the computer 101 determines an analysis module that will analyze a requested analysis item and then gives the relevant information to the computer 106 as well as the computer 102, 103, 104, or 105 of the determined analysis module.

Figure 2:
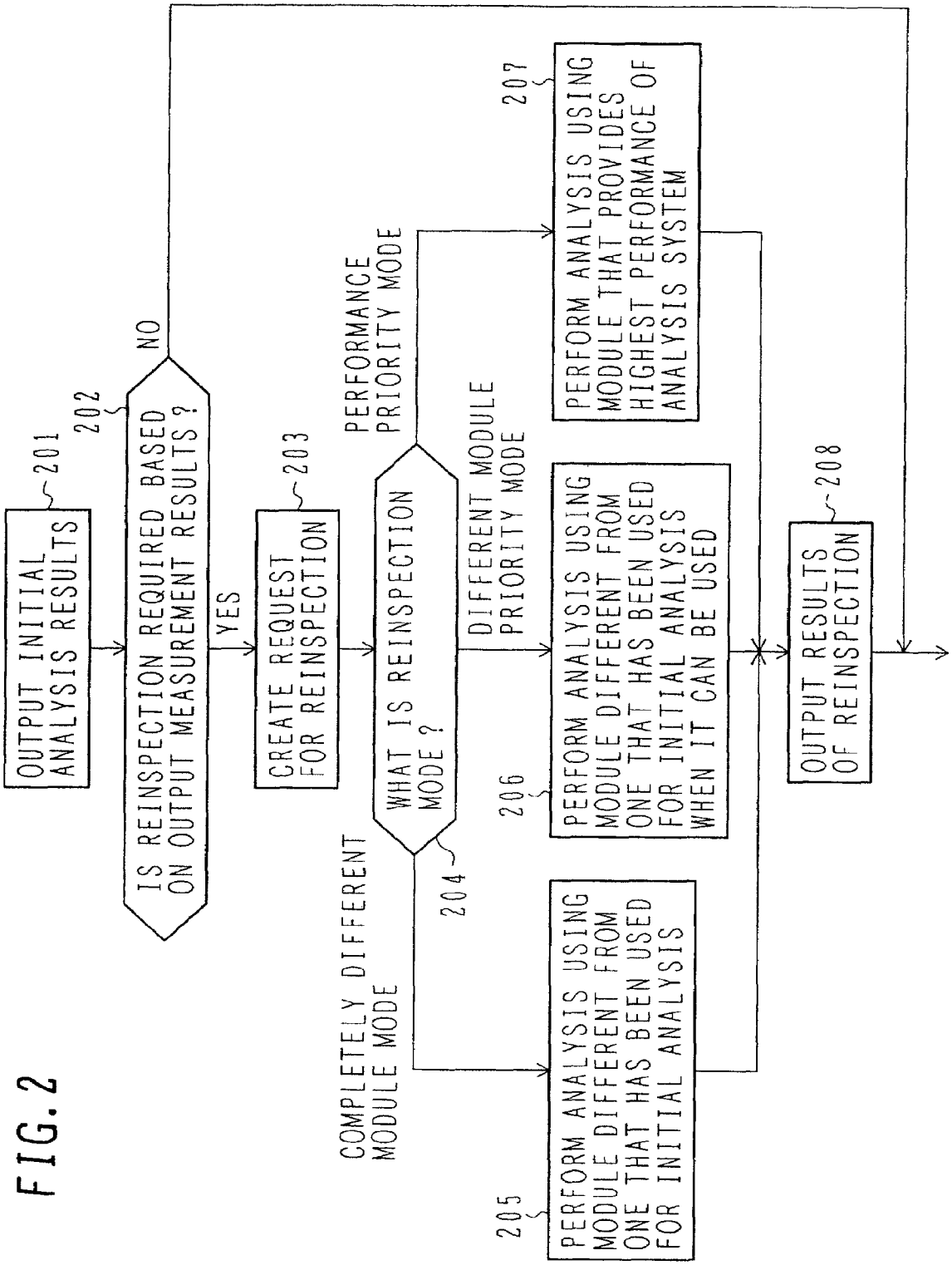
FIG. 2 is a diagram showing a processing flow from the start of analysis to the output of reinspection results according to an embodiment of the present invention.
Figure 3:
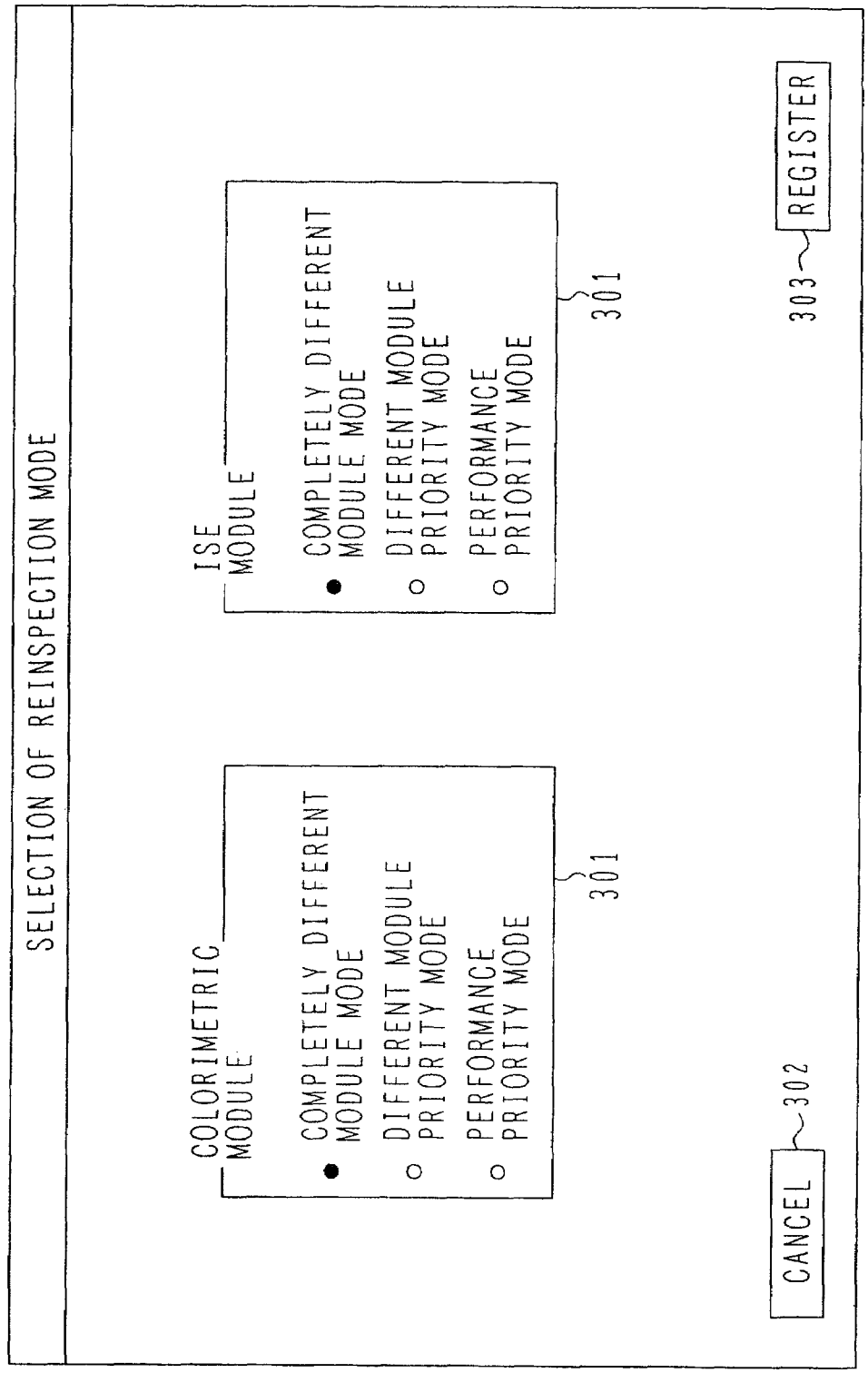
FIG. 3 is a diagram showing an example screen for making selection of reinspection mode with an I/O (input/output) apparatus of an automatic analyzer according to an embodiment of the present invention.

The following explains a case where any one of automatic analyzers different from one that has been used for initial analysis is to be used for reinspection of a sample in the automatic analysis system according to the present embodiment, with reference to FIG. 2 and FIG. 3.

FIG. 2 is a diagram showing a processing flow from the start of analysis to the output of reinspection results according to an embodiment of the present invention.

FIG. 3 is a diagram showing an example screen for making a selection of reinspection mode with an I/O apparatus of an automatic analyzer according to an embodiment of the present invention.

Before starting the analysis, an analysis method for reinspection of the same sample is set using the screen for making a selection of reinspection mode of FIG. 3. The reinspection mode is selected with a reinspection mode selection radio button 301.

Details of the reinspection mode will be explained below.

After selection of the reinspection mode, the Register button 303 is pressed to save settings or the Cancel button 302 to cancel the settings.

Although the reinspection mode has been set for each unit type in the above-mentioned example, it is also possible to set the same reinspection mode over the entire system.

During analysis operation, analysis is performed and then measurement results are outputted through any one analysis module (for example, the analysis module 5 of FIG. 1) in the analysis system in Step 201, as shown in FIG. 2.

In Step 202, the total management computer 101 performs analysis to determine whether each item is subjected to reinspection or not based on measurement results.

If none of items are subjected to reinspection, analysis of the sample is completed. If an item subject to reinspection occurs, the total management computer 101 creates a request for reinspection in Step 203.

In response to the request for reinspection, the apparatus may automatically perform the analysis or the operator may determine whether the analysis is actually to be performed.

When performing reinspection, therefore, a method of selecting an analysis module that will perform the reinspection depends on the reinspection mode selected by the reinspection mode selection radio button 301; the method being determined in Step 204.

In FIG. 3, a colorimetric module for measuring biochemical items and an ISE (electrolyte analysis) module for performing electrolyte analysis are illustrated as an example. Instead of these modules, however, an analysis module used for measurement of other items, such as an immunity analysis module, can also be used.

Step 205, a case where the completely different module mode has been selected with the reinspection mode selection radio button 301 will be explained below.

In this case, the carrier route of the sample rack is determined so that the analysis for reinspection is performed by any one of the analysis modules (the analysis modules 6, 7, and 8 of FIG. 1) different from the one (here, the analysis module 5 of FIG. 1) that has been used for the initial analysis stored in the total management computer 101 of FIG. 1, and the reinspection results are outputted in Step 208.

If it is not possible to analyze an item subject to reinspection by any one of the analysis modules different from the one that has been used for the initial analysis (for example, no reagent is provided in the reagent supply unit), the request for reinspection is canceled so as not to perform the analysis.

Step 206, a case where the different module priority mode has been selected with the reinspection mode selection radio button 301 will be explained below.

Like the case when the completely different module mode is selected, the carrier route of the sample rack is determined so that the analysis for reinspection is performed by any one of the analysis modules (the analysis modules 6, 7, and 8 of FIG. 1) different from the one (here, the analysis module 5 of FIG. 1) that has been used for the initial analysis stored in the total management computer 101 of FIG. 1, and the reinspection results are outputted in Step 208.

However, if it is not possible to analyze an item subject to reinspection by any one of the analysis modules different from the one that has been used for the initial analysis (for example, no reagent is provided in the reagent supply unit), reinspection is performed by the analysis module (here, the analysis module 5 of FIG. 1) that has been used for the initial analysis, and the measurement results are outputted in Step 208.

Step 207, a case where the performance priority mode has been selected with the reinspection mode selection radio button 301 will be explained below.

Without taking into consideration which analysis module has been used for the initial analysis when determining the carrier route of the sample rack at the time of reinspection, the sample rack is carried to an analysis module that provides the highest performance of the analysis system, reinspection is performed by the analysis module, and then the results are outputted in Step 208.

The use of the above-mentioned three different analysis modes makes it possible to provide a reinspection method that suits the policy of the operator and facility.

As mentioned above, reanalysis with another analysis module (automatic analyzer) is automatically performed by the control means according to the reinspection mode settings with an I/O apparatus. This makes it possible to perform reanalysis in shorter time than a case where the operator moves the sample to another analyzer and then performs the analysis.

Figure 4:
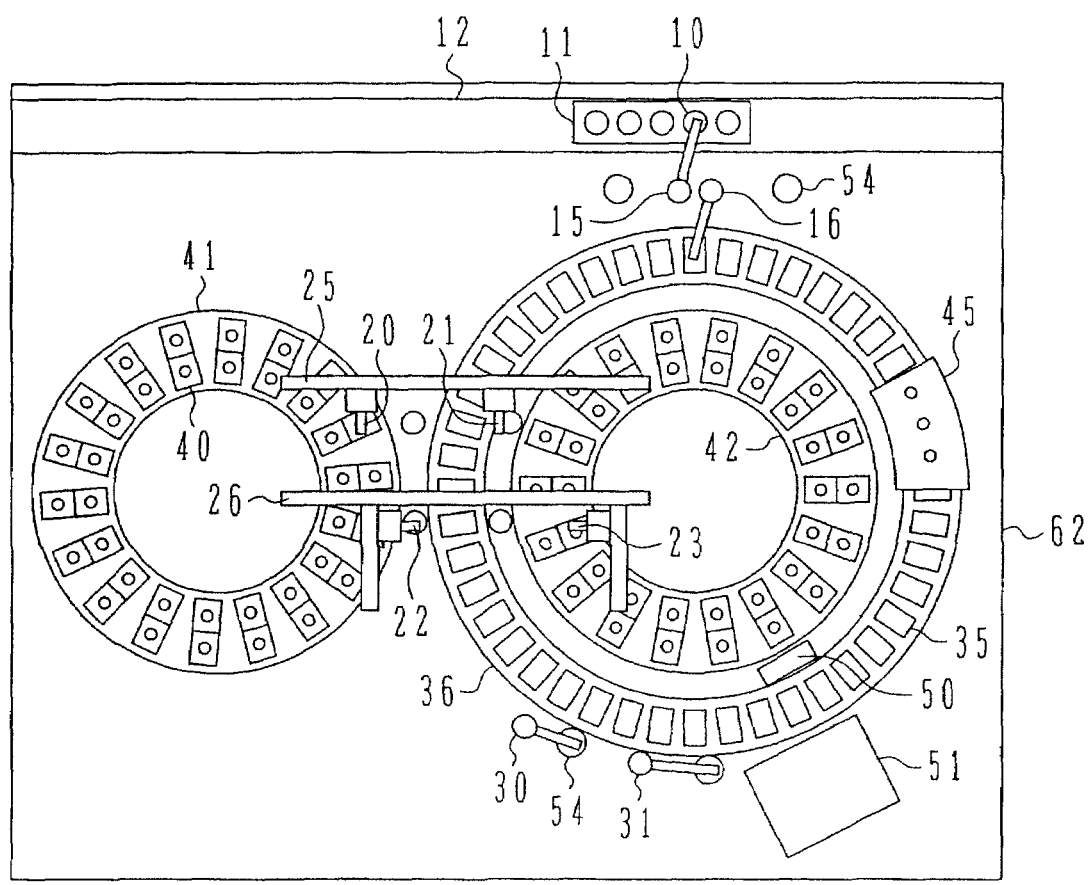
FIG. 4 is a diagram showing an example top view of an automatic analyzer according to another embodiment of the present invention.
Figure 5:
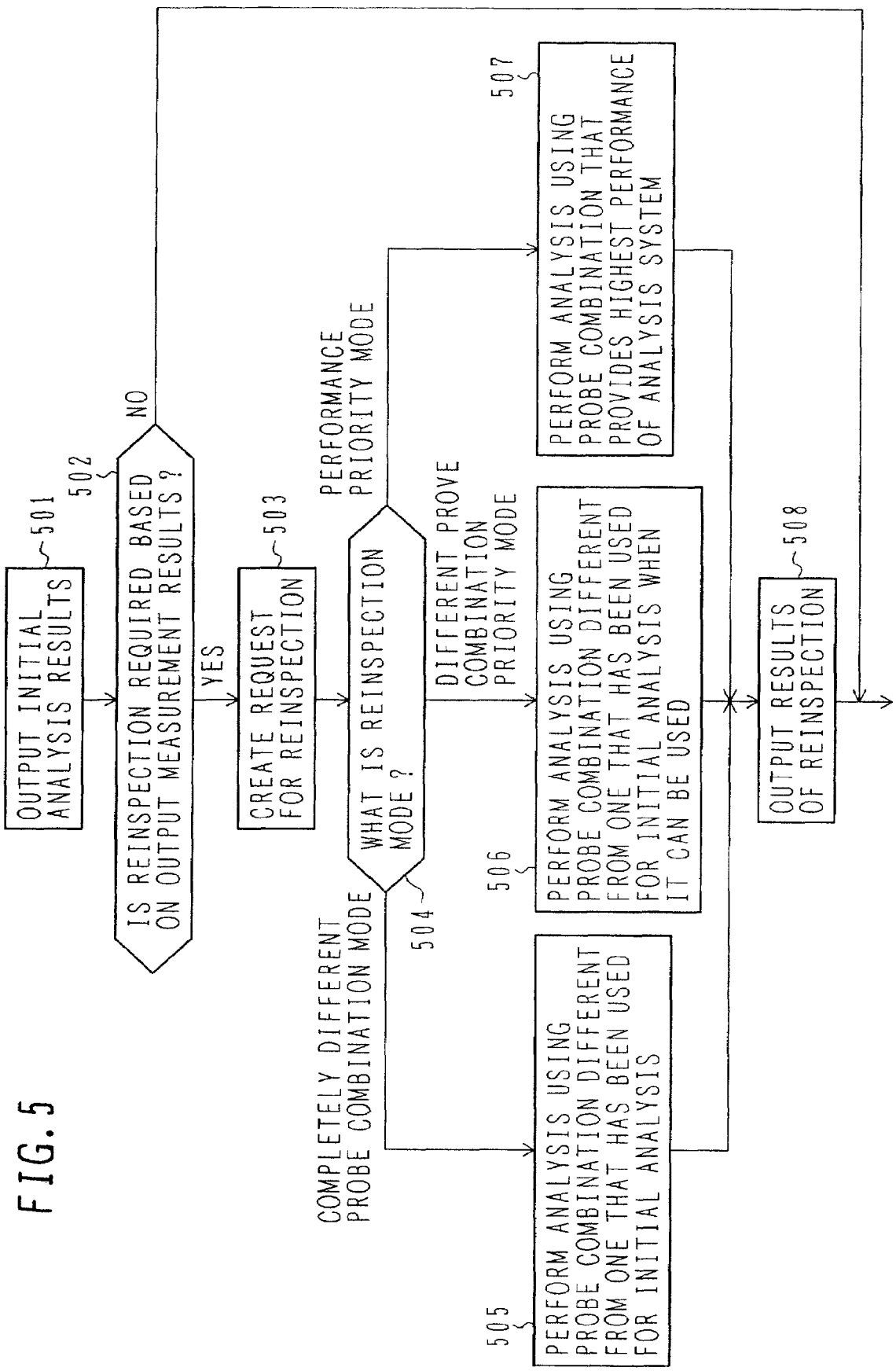
FIG. 5 is a diagram showing a processing flow from the start of analysis to the output of reinspection results according to another embodiment of the present invention.
Figure 6:
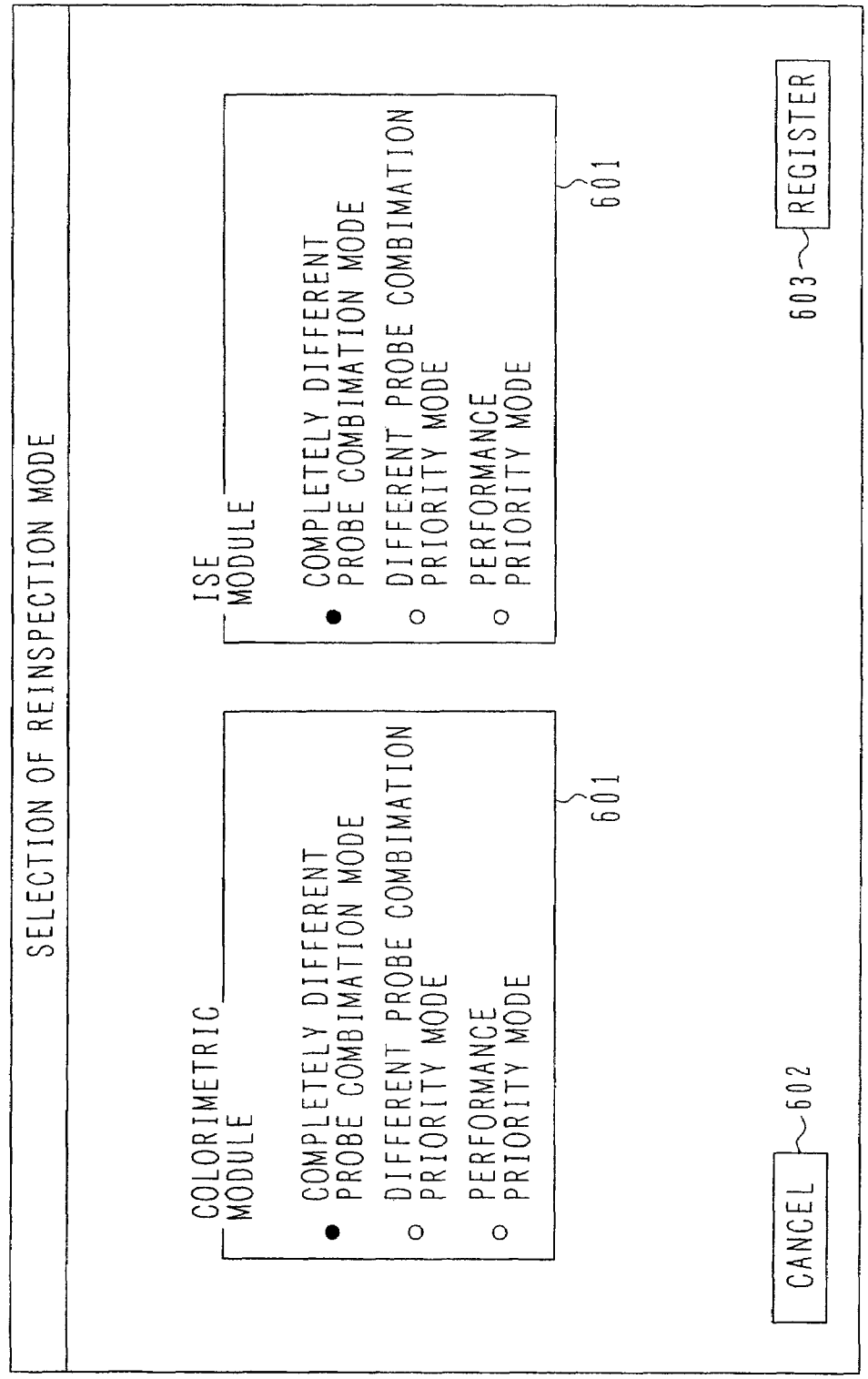
FIG. 6 is a diagram showing an example screen for making selection of an analyzer for reinspection with an I/O apparatus according to another embodiment of the present invention.

The following explains a case where the reagent vessels, the sample dispensing means, and the reagent dispensing means that have been used for the initial analysis are to be used for reanalysis of the sample in an automatic analyzer according to another embodiment, with reference to FIGS. 4, 5, and 6.

FIG. 4 is an example top view of an automatic analyzer for biochemical analysis.

A plurality of reaction vessels 35 are arranged along the circumference of a reaction disk 36 on a chassis 62 of the automatic analyzer. A reagent disk 42 is arranged inside the reaction disk 36, and a reagent disk 41 is outside. A plurality of reagent vessels 40 can be arranged along the circumference of each of the reagent disks 41 and 42.

Two reagents are placed in each reagent vessel 40. A carrier mechanism 12 for moving a sample rack 11 carrying sample vessels 10 close to the reaction disk 36 is installed.

Rails 25 and 26 are arranged on the reagent disks 41 and 42. Reagent probes 20 and 21 that can move in parallel with the rail 25 and vertically are located on the rail 25. Reagent probes 22 and 23 that can move in triaxial directions with the rail 26 are located on the rail 26.

The rails 25 and 26 and the reagent probes 20, 21, 22, and 23 are collectively referred to as reagent dispensing means.

Each of the reagent probes 20, 21, 22, and 23 is connected to a pump for reagent (not shown in FIG. 4).

Sample probes 15 and 16 that can rotate and move vertically are located between the reaction vessel 35 and the carrier mechanism 12. The sample probes 15 and 16 are referred to as sample dispensing means.

Each of the sample probes 15 and 16 is connected to a pump for samples (not shown in FIG. 4). Stirring apparatuses 30 and 31, a light source 50, an optical detecting apparatus 51, and a vessel cleaning mechanism 45 are arranged around the reaction disk 36.

The vessel cleaning mechanism 45 is connected to a pump for cleaning (not shown in FIG. 4). A cleaning port 54 is installed within an operating range of each of the sample probes 15 and 16, the reagent probes 20, 21, 22, and 23, and the stirring apparatuses 30 and 31.

A reagent storage for supplement (not shown in FIG. 4) is installed on the reagent disk 41. A plurality of reagent vessels 40 can be stored in the reagent storage for supplement.

Each of the pump for samples, the pump for reagent, the pump for cleaning (not shown in FIG. 4), the optical detecting apparatus 51, the reaction vessel 35, the reagent disk 41, the reagent probes 20, 21, 22, and 23, and the sample probes 15 and 16 is connected to a controller (not shown in FIG. 4).

The sample rack 11 is guided by the carrier mechanism 12. Being supported by the sample rack 11, a sample positioned at a sample inhalation position is inhaled by the sample probes 15 and 16 and then thrown out to a reaction vessel 35 on the reaction disk 36 at a sample dispensing position.

The reaction vessel 35 to which the sample has been thrown out is moved to a first reagent dispensing position through the rotation of the reaction disk 36. Then, at this position the reagent in the reagent vessels 40 supported by the reagent disk 41 or 42 is dispensed in the reaction vessel 35 through the first reagent probes 20 or 21.

The reaction vessel 35 in which the first reagent was dispensed is moved to a stirring position. Then, at this position the sample and the first reagent are stirred by the stirring apparatus 30 or 31.

Furthermore, if a second reagent needs to be added, the reaction vessel 35 in which stirring has been completed is moved to a second reagent dispensing position. Then, at this position the second reagent in the reagent vessels 40 supported by the reagent disk 41 or 42 is dispensed in the reaction vessel 35 through the second reagent probes 22 or 23.

The reaction vessel 35 in which dispensing has been completed is moved to the stirring position. Then, at this position the sample and the first and second reagents are stirred in the reaction vessel 35 by the stirring apparatus 30 or 31 to create a relevant reaction liquid.

The reaction vessel 35 containing the reaction liquid is moved to a measurement position. Then, at this position the reaction liquid is subjected to multi-wavelength absorbance measurement by the optical detecting apparatus 51 to obtain analysis results.

FIG. 5 is a diagram showing a processing flow from the start of analysis to the output of reinspection results in an automatic analyzer of another aspect of the invention.

FIG. 6 is a diagram showing an example screen for making selection of analyzer for reinspection with an I/O apparatus of an automatic analyzer of another aspect of the invention.

Before starting the analysis, an analysis method for reinspection of the same sample is set using the screen for making a selection of a reinspection mode of FIG. 6. The analysis mode for reinspection is selected with a reinspection mode selection radio button 601.

Details on the reinspection mode will be explained below.

After selection of the reinspection mode, the Register button 603 is pressed to save the settings or the Cancel button 602 to cancel the settings.

Although the reinspection mode has been set for each unit type in the above-mentioned example, it is also possible to set the same reinspection mode over the entire system.

During analysis operation, the sample is inhaled by the above-mentioned sample probe 15 or 16 of FIG. 4 at the sample inhalation position in Step 501 and then thrown out to the reaction vessel 35, as shown in FIG. 4.

The reagent in the reagent vessels 40 supported by the reagent disk 41 or 42 is dispensed in the reaction vessel 35 through the first reagent probes 20 or 21.

If a second reagent needs to be added, the reaction vessel 35 is moved to a second reagent dispensing position. Then, at this position the second reagent in the reagent vessels 40 supported by the reagent disks 41 or 42 is dispensed in the reaction vessel 35 through the second reagent probes 22 or 23.

Specifically, analysis of one item is performed by use of up to one sample probe and two reagent probes.

Sample probes and reagent probes used for analysis of one item are collectively referred to as analysis probes. (In the present analysis, for example, it is assumed that the sample probe 15 and the reagent probes 20 and 22 are used.) Initial analysis results are outputted by use of the above-mentioned analysis probes.

In Step 502, analysis is performed to determine whether each measured item is subjected to reinspection or not based on measurement results. If none of the items are subject to reinspection, analysis of the sample is completed; otherwise, a request for reinspection is created in Step 503.

In response to the request for reinspection, the apparatus may automatically perform the analysis or the operator may determine whether the analysis is actually to be performed.

When performing reinspection, therefore, a method of selecting an analysis probe to be used for reinspection depends on the reinspection mode selected by the reinspection mode selection radio button 601; the method being determined in Step 504.

Step 505, a case where the completely different analysis probes mode has been selected with the reinspection mode selection radio button 601 will be explained below.

In this case, analysis scheduling is determined so that analysis for reinspection of the same sample be performed by any one of the analysis probes (here, the sample probe 16 and the reagent probes 21 and 23) different from the one (here, the sample probe 15 and the reagent probes 20 and 22) that has been used for the initial analysis stored in the apparatus, and the reinspection results are outputted in Step 508.

If it is not possible to analyze an item subject to reinspection by any one of the analysis probes different from the one that has been used for the initial analysis, the request for reinspection is canceled so as not to perform the analysis.

Step 506, a case where the different analysis probes priority mode has been selected with the reinspection mode selection radio button 601 will be explained below.

Like the case when the completely different analysis probes mode is selected, analysis scheduling is determined so that the analysis for reinspection of the same sample is performed by any one of the analysis probes (here, the sample probe 16 and the reagent probes 21 and 23) different from one (here, the sample probe 15 and the reagent probes 20 and 22) that has been used for the initial analysis stored in the apparatus, and the reinspection results are outputted in Step 508.

However, if it is not possible to analyze an item subject to reinspection by any one of the analysis modules different from the one that has been used for the initial analysis, reinspection is performed by the analysis module (the sample probe 15 and the reagent probes 20 and 22) that has been used for the initial analysis, and the analysis results are outputted in Step 508.

Step 507, a case the performance priority mode has been selected with the reinspection mode selection radio button 601 will be explained below.

Without taking into consideration which analysis probe has been used for the initial analysis when determining analysis scheduling at the time of reinspection, analysis scheduling is performed so as to use the analysis probe that provides highest performance of the analyzer, reinspection is performed with the analysis probes, and then the results are outputted in Step 508.

Although an independent analyzer having one or a plurality of sample supply units and one or a plurality of reagent supply units has been explained, the present embodiment is also applicable to an analysis system having a plurality of the present analyzers.

As mentioned above, reanalysis of the sample is automatically performed by control means by use of a reagent in a reagent vessel different from the one, the sample dispensing means, and the reagent dispensing means that have previously been used. This makes it possible to perform reanalysis in shorter time than the case where the operator moves the sample to another analyzer and then performs the analysis.

This also makes it possible to avoid analysis failure caused by reagent and apparatus involved in reanalysis using the same reagent, the same sample dispensing means, and the same reagent dispensing means.

Figure 7:
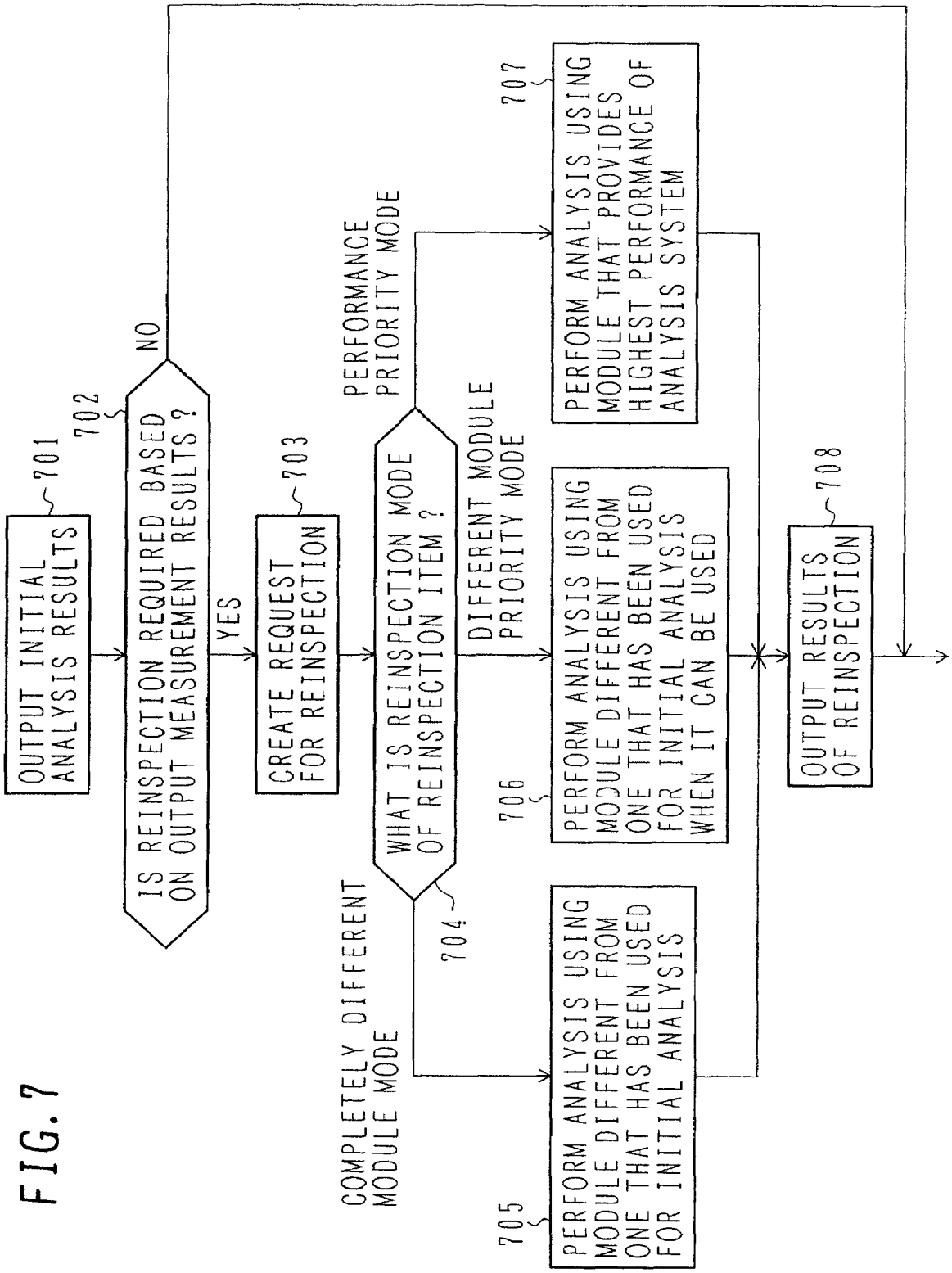
FIG. 7 is a diagram showing a processing flow from the start of analysis to the output of reinspection results in an automatic analyzer according to an embodiment of the present invention.
Figure 8:
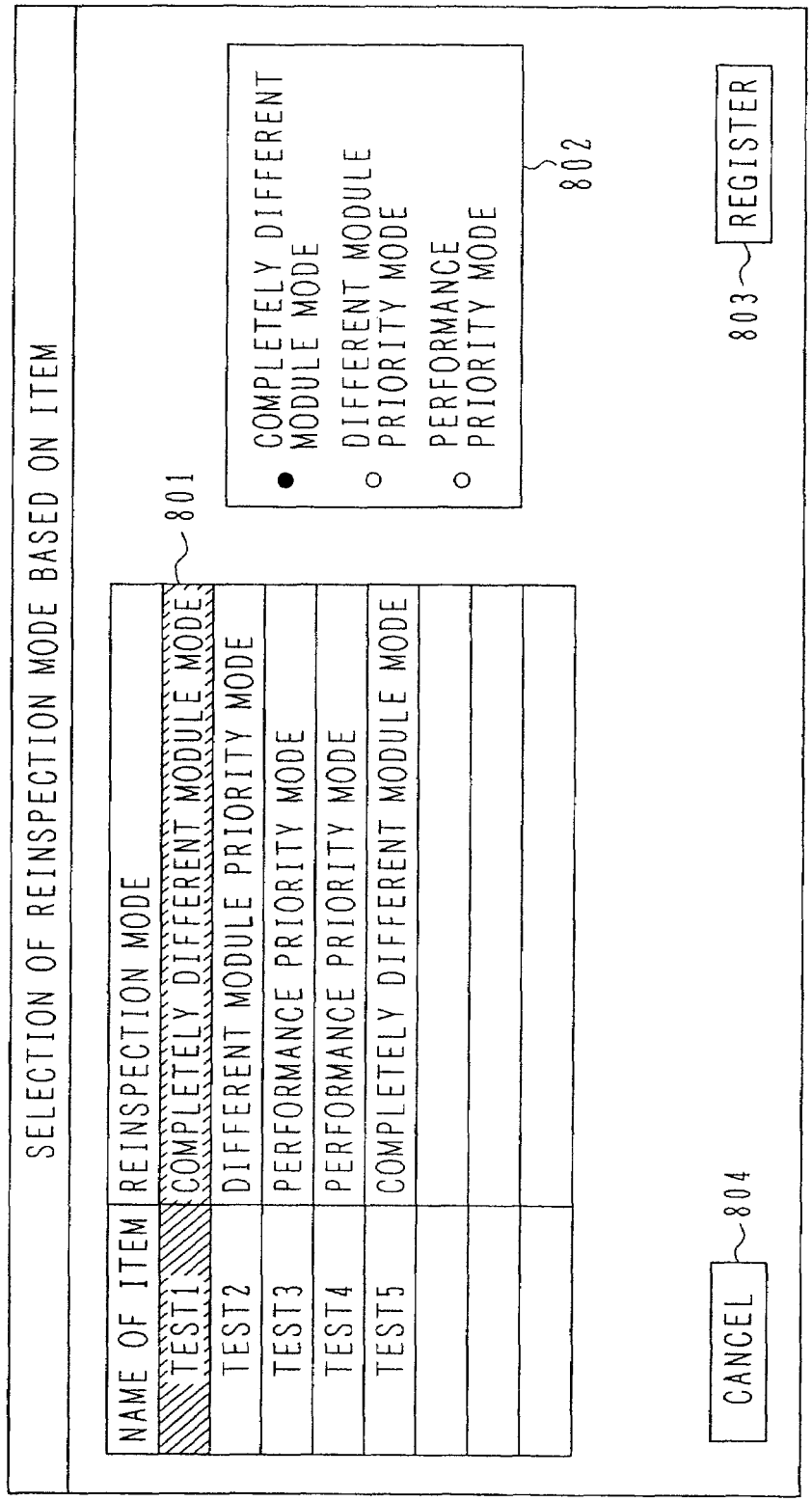
FIG. 8 is a diagram showing an example screen for making selection of reinspection mode based on item with an I/O apparatus of an automatic analyzer according to an embodiment of the present invention.

The following explains a method of selecting the analyzer used based on the reinspection item at the time of reinspection, with reference to FIG. 7 and FIG. 8.

Although the present embodiment is similarly applicable to an analysis system which includes a plurality of analysis modules as shown in FIG. 1 and an apparatus which includes a plurality of analysis probes in one automatic analyzer as shown in FIG. 4, the present embodiment will be explained with reference to FIG. 1 as an example.

FIG. 7 is a diagram showing a processing flow from the start of analysis to the output of reinspection results in an automatic analyzer according to an embodiment of the present invention.

FIG. 8 is a diagram showing an example screen for making selection of reinspection mode based on item with an I/O apparatus of an automatic analyzer according to an embodiment of the present invention.

Before starting analysis, the reinspection mode at the time of reinspection is set for each item on the screen for making selection of reinspection mode based on item in FIG. 8.

The reinspection mode can be set for each item by selecting an item displayed in an item list 801 and then selecting an analysis mode for reinspection with a reinspection mode selection radio button 802.

Details of the reinspection mode will be explained below.

After selection of the reinspection mode, the Register button 803 is pressed to save the settings or the Cancel button 804 to cancel the settings.

During analysis operation, analysis results are obtained in any one analysis module (for example, the analysis module 5 of FIG. 1) in the analysis system in Step 701, as shown in FIG. 7.

In Step 702, the total management computer 101 performs analysis to determine whether each measured item is subjected to reinspection or not based on measurement results.

If none of items are subject to reinspection, analysis of the sample is completed; otherwise, the total management computer 101 creates a request for reinspection in Step 703.

In response to the request for reinspection, the apparatus may automatically perform analysis or, in spite of the issuance of the request for reinspection, the operator may determine whether analysis is actually to be performed or not.

The method of selecting the analysis module that will perform reinspection depends on the reinspection mode selected for an item judged as needing to be reinspected on the screen for making selection of reinspection mode based on the item in FIG. 7 in Step 704.

Step 705, a case where an item (for example, Test 1 of FIG. 8), for which the completely different module mode has been selected with the reinspection mode selection radio button 802, is subjected to reinspection will be explained below.

In this case, the carrier route of the sample rack is determined so that the analysis for reinspection of Test 1 is performed by any one of analysis modules (the analysis modules 6, 7, and 8 of FIG. 1) different from the one (here, the analysis module 5 of FIG. 1) that has been used for the initial analysis stored in the total management computer 101 of FIG. 1, and the reinspection results are outputted in Step 708.

If it is not possible to analyze an item subject to reinspection by any one of the analysis modules different from the one that has been used for the initial analysis (for example, no reagent is provided in the reagent supply unit), the request for reinspection is canceled so as not to perform the analysis.

Step 706, a case where an item (for example, Test 2 of FIG. 8), for which the different module priority mode has been selected with the reinspection mode selection radio button 802, is subjected to reinspection will be explained below.

Like the case when the completely different module mode is selected, the carrier route of the sample rack is determined so that the analysis for the reinspection of Test 2 is performed by any one of the analysis modules (the analysis modules 6, 7, and 8 of FIG. 1) different from the one (here, the analysis module 5 of FIG. 1) that has been used for the initial analysis stored in the total management computer 101 of FIG. 1, and the reinspection results are outputted in Step 708.

However, if it is not possible to analyze an item subject to reinspection by any one of the analysis modules different from one that has been used for initial analysis (for example, no reagent is provided in the reagent supply unit (reagent vessels)), reinspection is performed by the analysis module (here, the analysis module 5 of FIG. 1) that has been used for the initial analysis, and the measurement results are outputted in Step 708.

Step 707, a case where an item (for example, Test 3 of FIG. 8), for which the performance priority mode has been selected with the reinspection mode selection radio button 802, is subject to reinspection will be explained below.

Without taking into consideration which analysis module has been used for the initial analysis when determining the carrier route of the sample rack at the time of reinspection, the sample rack is carried to the analysis module which provides the highest performance of the analysis system, reinspection is performed by the analysis module, and then the results are outputted in Step 708.

Figure 9:
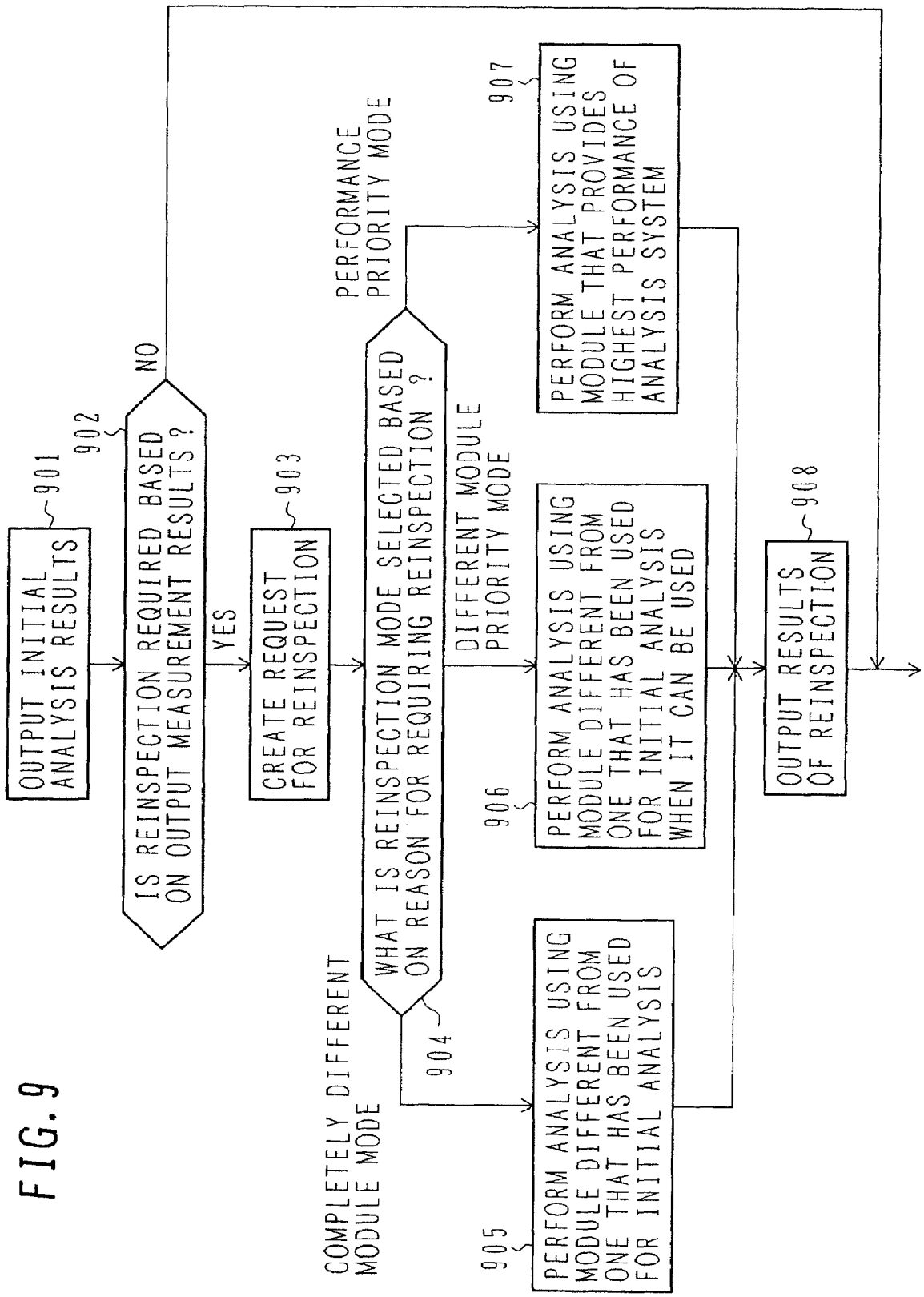
FIG. 9 is a diagram showing a processing flow from the start of analysis to the output of reinspection results in an automatic analysis system according to another embodiment of the present invention.
Figure 10:
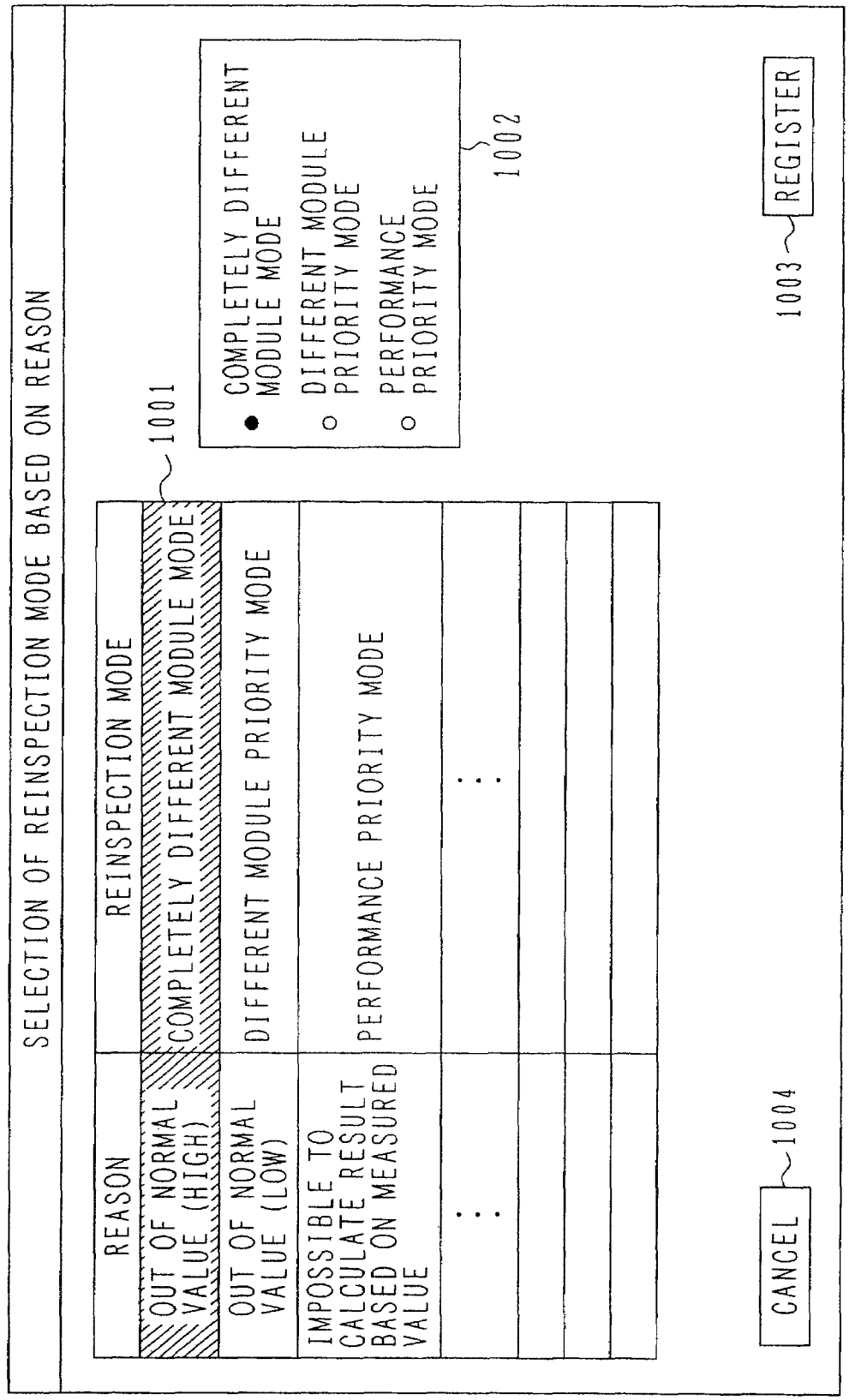
FIG. 10 is a diagram showing an example screen for making selection of reinspection mode based on reason with an I/O apparatus of an automatic analyzer according to an embodiment of the present invention.

The following explains a method of selecting the analyzer used according to the reason for reinspection at the time of reinspection in an automatic analysis system according to another embodiment, with reference to FIG. 9 and FIG. 10.

Although the present embodiment is similarly applicable to an analysis system which includes a plurality of analysis modules as shown in FIG. 1 and an apparatus which includes a plurality of analysis probes in one analyzer as shown in FIG. 4, the present embodiment will be explained with reference to FIG. 1 as an example.

FIG. 9 is a diagram showing a processing flow from the start of analysis to the output of reinspection results in an automatic analysis system according to a different embodiment of the present invention.

FIG. 10 is a diagram showing an example screen for making selection of reinspection mode based on reason with an I/O apparatus of an automatic analyzer according to an embodiment of the present invention.

Before starting analysis, the reinspection mode at the time of reinspection is set in the screen for making selection of reinspection mode based on reason in FIG. 10.

It is possible to set the reinspection mode based on reason of reinspection by selecting a reason from the ones displayed in a list of reasons of reinspection 1001 (showing a case when measured value is higher than a normal value, a case when measured value is lower than a normal value, and a case when it is impossible to calculate result based on measured value) and then selecting an analysis mode for reinspection with the reinspection mode selection radio button 1002.

Details of the reinspection mode will be explained below.

After selection of the reinspection mode, the Register button 1003 is pressed to save the settings or the Cancel button 1004 to cancel the settings.

During analysis operation, analysis results are obtained in any one analysis module (for example, the analysis module 5 of FIG. 1) in the analysis system in Step 901.

In Step 902, the total management computer 101 performs analysis to determine whether each measured item is subjected to reinspection or not based on measurement results. If none of items are subject to reinspection, analysis of the sample is completed.

Otherwise (if any item is subject to reinspection), the total management computer 101 creates a request for reinspection in Step 903.

In response to the request for reinspection, the apparatus may automatically perform analysis or, in spite of the issuance of the request for reinspection, the operator may determine whether analysis is actually to be performed or not.

The method of selecting the analysis module that will perform reinspection depends on the reinspection mode selected for an item judged as needing to be reinspected on the screen for making the selection of the reinspection mode based on reason in FIG. 10 in Step 904.

Step 905, a case where reinspection is performed based on a reason and the completely different module mode has been selected with the reinspection mode selection radio button 1002 (corresponding, for example, to "Out of normal value (high)" of FIG. 10) will be explained below.

In this case, the carrier route of the sample rack is determined so that analysis for reinspection based on reason "Out of normal value (high)" is performed by any one of the analysis modules (here, the analysis modules 6, 7, and 8 of FIG. 1) different from the one (here, the analysis module 5 of FIG. 1) that has been used for the initial analysis stored in the total management computer 101 of FIG. 2, and the reinspection results are outputted in Step 908.

If it is not possible to analyze an item subject to reinspection by any one of the analysis modules different from the one that has been used for the initial analysis (for example, no reagent is provided in the reagent supply unit), the request for reinspection is canceled so as not to perform the analysis.

step 906, a case when reinspection is performed based on a reason and the different module priority mode has been selected with the reinspection mode selection radio button 1002 (corresponding, for example, to "Out of normal value (low)" of FIG. 10) will be explained below.

Like the case when the completely different module mode is selected, the carrier route of the sample rack is determined so that the analysis for reinspection based on reason "Out of normal value (low)" is performed by any one of analysis modules (the analysis modules 6, 7, and 8 of FIG. 1) different from the one (here, the analysis module 5 of FIG. 1) that has been used for the initial analysis stored in the total management computer 101 of FIG. 1, and the reinspection results are outputted in Step 908.

However, if it is not possible to analyze an item subject to reinspection by any one of the analysis modules different from the one that has been used for the initial analysis (for example, no reagent is provided in the reagent supply unit), reinspection is performed by the analysis module (here, the analysis module 5 of FIG. 1) that has been used for initial analysis, and the measurement results are outputted in Step 908.

Step 907, a case where reinspection is performed based on a reason and the performance priority mode has been selected with the reinspection mode selection radio button 1002 (corresponding, for example, to "Impossible to calculate result based on measured value" of FIG. 10) will be explained below.

Without taking into consideration which analysis module has been used for the initial analysis when determining the carrier route of the sample rack at the time of reinspection, the sample rack is carried to the analysis module that provides the highest performance of the analysis system, reinspection is performed by the analysis module, and then the results are outputted in Step 908.

What is claimed is:

1. An automatic analysis system comprising:
   a sample rack holding a sample vessel containing a sample;
   a carrier line on which said sample rack is carried;
   a plurality of automatic analyzers arranged along said carrier line;
   a display unit; and
   a total management computer configured to control said carrier line to carry said sample rack to a selected one of said plurality of automatic analyzers,
   said total management computer including a processor and a storage means that stores a plurality of re-inspection modes, the plurality of re-inspection modes including;
      a first re-inspection mode that executes re-inspection of a sample which is determined to require re-inspection using a second one of the plurality of automatic analyzers that is different from the first one of the plurality of automatic analyzers that performed an initial analysis of the sample,
      a second re-inspection mode that executes re-inspection of the sample which is determined to require re-inspection by use of one of the plurality of automatic analyzers which is determined to provide the highest performance of the system, which highest performing automatic analyzer has the least number of abnormal results, as determined by the total management computer over time; and
      a third re-inspection mode that executes the re-inspection of the sample which is determined to require re-inspection, by again using a second one of the plurality of automatic analyzers, when the second one of the plurality of automatic analyzers is able to analyze the sample, however, when the second one of the plurality of automatic analyzer is not available, then re-inspection is performed by the first automatic analyzer of the plurality of automatic analyzers that performed the initial analysis of the sample,
   the processor being configured to execute, using the information from the storage means, the following steps in order:
   a) displaying on the display unit a re-inspection mode selection radio button that a user is able to use to select one of the first, second, and third re-inspection modes, wherein the computer saves the selected re-inspection mode;
   b) providing the sample contained in the sample vessel of the sample rack at a first one of the plurality of automatic analyzers to perform the initial analysis of the sample, the initial analysis results being outputted to the total management computer;
   c) determining whether the sample in the sample rack requires re-inspection when the initial analysis results of the sample in the sample vessel are judged to be an abnormal value in comparison with a normal value by the total management computer;
   d) controlling the carrier line to carry the sample rack holding the sample vessel to a determined re-inspection location, based upon the re-inspection mode selected in step a), upon determination of the abnormal value in the sample in the first of the plurality of automatic analyzers; and
   e) outputting the results of the re-inspection to the total management computer.

* * * * *